United States Patent [19]

Dallatomasina et al.

[11] Patent Number: 4,549,987
[45] Date of Patent: Oct. 29, 1985

[54] ASPARTAME SYNTHESIS

[75] Inventors: Franco Dallatomasina, Segrate; Roberto Ortica, Rozzano; Pietro Giardino; Ernesto Oppici, both of Milan, all of Italy

[73] Assignee: Farmitalia Carlo Erba S.p.A., Milan, Italy

[21] Appl. No.: 637,786

[22] Filed: Aug. 6, 1984

[30] Foreign Application Priority Data

Aug. 12, 1983 [GB] United Kingdom ................ 8321802

[51] Int. Cl.$^4$ .......................................... C07C 103/52
[52] U.S. Cl. .......................................... 260/112.5 R
[58] Field of Search ................................ 260/112.5 R

[56] References Cited

U.S. PATENT DOCUMENTS 3,492,131  1/1970  Schlatter .................... 260/112.5 R
3,798,206  3/1974  Uchiyama et al. ........... 260/112.5 R
4,071,511  1/1978  Takemoto et al. .......... 260/112.5 R

FOREIGN PATENT DOCUMENTS 0058063  8/1982  European Pat. Off. .

Primary Examiner—Delbert R. Phillips
Assistant Examiner—F. T. Moezie
Attorney, Agent, or Firm—Oblon, Fisher, Spivak, McClelland & Maier, P.C.

[57] ABSTRACT

A process for deformylation and separation of N-formyl-L-α-aspartyl-L-phenylalanine methyl ester from a mixture containing both α and β isomers thereof, which comprises admixing with said isomeric mixture hydrogen peroxide and an organic acid.

9 Claims, No Drawings

ASPARTAME SYNTHESIS

BACKGROUND OF THE INVENTION

1. Field of the Invention

The present invention relates to a new synthesis for aspartame, i.e., L-αaspartyl-L-phenylalanine methyl ester.

2. Description of Prior Art

Aspartame has sweetening properties similar to cane and beet sugar, and is used as a sweetening agent for foods and beverages, see for instance, U.S. Pat. No. 3,492,131.

Aspartame is a dipeptide, and, as such, is formed with an amide bond between an activated carboxyl group of the amino acid and the amino group of another amino acid. Activation is necessary to increase the rate and the yield of the condensation. In carrying out the formation process, the desired pure peptide requires the protection of all other functional groups not involved in the peptide bond formation, which means that after formation, the protecting groups must be removed. For instance, aspartame is known to be prepared by the reaction of an N-protected-L-aspartic anhydride with an L-phenylalanine methyl ester to yield a mixture of L-α-aspartyl-L-phenylalanine methyl ester and L-β-aspartyl-L-phenylalanine methyl ester. The N-protecting groups used are the common N-protecting groups in peptide chemistry, for example benzyloxycarbonyl or a formyl group. N-deprotection is then carried out in presence of strong acids (U.S. Pat. No. 4,071,511). or in the presence of hydroxylamine (U.S. Pat. No. 4,021,418). Neither of these methods are entirely suitable for industrial purposes, however. Deformylation results in low yields, requires expensive reagents, and often results in esterification of the β-carboxy group, or hydrolysis of the ester or peptide bond. Moreover, the above process requires the further step of separating the α- and β-isomers (the β-isomer does not have sweetening properties), which leads to a cost increase.

It would be desirable to provide for an industrial process for the production of aspartame wherein the deformylation will occur with such selectivity that side reactions such as hydrolysis of the ester or of the peptide bond is minimized.

SUMMARY OF THE INVENTION

According to the present invention, aspartame is isolated from a reaction mixture of N-formyl-L-α, β-aspartyl-L-phenylalanine methyl ester by admixing therewith hydrogen peroxide, and an organic acid. In a further embodiment of this invention, a mineral acid is also admixed therewith.

DETAILED DESCRIPTION OF THE INVENTION

It has now been found that, if to the reaction mixture containing N-formyl aspartame, aqueous hydrogen peroxide solution of from 10 to 90% wt. an organic acid and preferably an aqueous mineral acid solution are added, deformylation will occur selectively with a minimal occurrence of side reactions, such as hydrolysis of the ester or of the peptide bond.

Suitable organic acids which can be used in the present process include the carboxylic acids of the formula R—COOH wherein R is hydrogen, $C_1$–$C_3$ alkyl, phenyl or substituted phenyl, wherein said substituent may be one or more of lower ($C_1$–$C_4$) alkyl, chloro or cyano. Best results are obtained with formic or m-chlorobenzoic acid.

The hydrogen peroxide is used in an amount of from 1 to 6 mole of the formyl group.

It is quite desirable to add at least one mineral acid to the mixture. Suitable acids are those having a first dissociation constant of not less than $1.5 \times 10^{-2}$ at 25° C., such as, but not limited to, the conventional mineral acids such as phosphoric, hydrochloric and sulphuric acid.

The total of organic and mineral acids in the mix is desirably in an amount of from 0.5 to 10 moles per mole of N-formyl-aspartame in the reaction mixture.

The reaction temperature may be in a range of from 10° C. to the boiling point of the mixture, and the reaction time range is from 2 to 40 hours.

The condensation mixture to which the deformylating agents of the present invention are added is formed by solvents such as ethylacetate, dichloroethane, methylethylketone or acetic acid.

To separate the desired aspartame, the reaction mixture may, after cooling, be diluted with water; the aqueous phase separated and adjusted to pH of about 4.5–5 with the use of an alkali, such as sodium carbonate or bicarbonate, ammonium or sodium hydroxide. The aspartame which precipitates is then collected by the usual means, such as filtration.

The process according to the invention offers several advantages over the conventional prior art processes. For one, it is not necessary to isolate the N-formyl-L-α,β-aspartyl-L-phenylalanine methyl ester from the reaction mixture in which it is prepared prior to deformylation. The separation of the isomers is accomplished in the same step as the deformylation, by virtue of the precipitation of the aspartame alone and not the β-isomer.

Moreover, the particular reaction conditions of the process of the invention avoid the risks of splitting the peptide bond, esterifying the β-carbonyl group, removal of the esterifying methyl group or formation of the undesired by-product diketopiperazine.

Better isolation yields are achieved as compared to the conventional prior art processes characterized by acid or basic hydrolysis and the process is suitable for commercial application.

The invention will now be illustrated by the following examples, which are provided herein for purposes of illustration only and are not intended to be considered as limiting of the invention unless otherwise specifically so stated.

EXAMPLE 1

40 ml. aqueous 40% hydrogen peroxide, 20 ml. of formic acid and 40 ml. of 37% aqueous hydrochloric acid were added at room temperature to a solution of 100 g of N-formyl-α,β-L-aspartyl-L-phenylalanine methyl ester (α,β-isomer ratio 8:2) in 160 ml. of dichloroethane and 40 ml. of acetic acid.

The mixture was heated at 45° C. for eight hours and then cooled. The content of the reaction mixture by analysis HPLC (high pressure liquid chromatography) is:

α-L-aspartyl-L-phenylalanine methyl ester (abbrev. αAPM) 231 mg/ml

β-L-aspartyl-L-phenylalanine methyl ester (abb. βAPM) 56.6 mg/ml

N-formyl-α-L-aspartyl-L-phenylalanine methyl ester (abb. αFAPM) 18 mg/ml
N-formyl-β-L-aspartyl-L-phenylalanine methyl ester (abb. βFAPM) 4.6 mg/ml The analytical conditions are as follows:
Column:
Lichrosorb RP 1.8 5 μm (Knauer)
Length=250 mm
Int. diam.=4.6 mm
Eluent/Mixture of phosphate buffer (ph=3.0±0.1) and acetonitrile (87:13 V/V)
(composition of buffer: 3.4 g of $KH_2PO_4$ dissolved in 1 liter of water and adjusted to pH with $H_3PO_4$).
flow rate: 1.5 ml/min
T column: 35° C.

The period of retention time of α-aspartyl-L-phenylalanine methyl ester: is about 800 sec.

Yield of α-L-aspartyl-L-phenylalanine methyl ester is 68 g (93%). The reaction mixture was diluted with ml 500 of water the aqueous layer was separated, the pH was adjusted to 4.5 with 20% aqueous sodium hydroxide, stirred for one hour at room temperature and cooled. The free aspartame was precipitated and was collected by filtration. 45.5 g of pure compound were obtained in 70% yield m.p. 233°–235° C. (with decomposition).

$[\alpha]_D^{22} = 33.2$ (C=1, acetic acid).

Title HPLC>99%.

EXAMPLE 2

80 ml of aqueous hydrogen peroxide, 40%, 60 ml of formic acid and 20 ml of 96% sulfuric acid were added at 10° C. to a solution of 100 g of N-formyl- α,β-L-aspartyl-L-phenyl-alanine methylester (α,β-isomer ratio 8/2) in 300 ml of ethylacetate and 40 ml of acetic acid.

After 24 hours at 10° C., the content of the reaction mixture by analysis HPLC is:

| | |
|---|---|
| α APM | 126.9 mg/ml |
| β APM | 31.5 mg/ml |
| α FAPM | 20.6 mg/ml |
| β FAPM | 5.2 mg/ml |

Yield of α-L-aspartyl-L-phenyl alanine methylester is 63.5 g (86.9%). Operating as in Example 1, the aspartame was obtained in 65% yield.

EXAMPLE 3

Operating as in Example 1, but using 40 ml of acetic acid instead of formic acid (60° C. for eight hours), the aspartame was obtained in 68% yield.

EXAMPLE 4

Operating as in Example 1, but using 30 ml of 85% aqueous phosphoric acid instead of 37% aqueous hydrochloric acid: (45° C. for eight hours) the aspartame was obtained in 72% yield.

EXAMPLE 5

Operating as in Example 4, but using 60 ml of 40% aqueous hydrogen peroxide instead of 40 ml aqueous hydrogen peroxide (25° C. twenty hours) the aspartame was obtained in 70% yield.

EXAMPLE 6

40 ml of 60% aqueous hydrogen peroxide and 73 g of 3-chlorobenzoic acid were added at 20° C. to a solution of 100 g of N-formyl-α,β-L-aspartyl-L-phenyl alanine methyl ester (α/β-isomer ratio 8:2) in 160 ml of dichloroethane and 40 ml of acetic acid.

The reaction mixture was stirred at 20° C. for 24 hours.

With the working-up as in Example 1, the aspartame is obtained in 64% yield.

Having now fully described the invention, it will be apparent that many modifications can be readily made thereto without departing from the spirit or scope thereof.

What is claimed as new and desired to be secured by Letters Patent of the United States is:

1. A process for deformylating and separating N-formyl-L-α-aspartyl-L-phenylalanine methyl ester from a mixture containing both α and β isomers thereof, which comprises admixing with said isomeric mixture hydrogen peroxide; an organic acid of the formula R—COOH, wherein R is hydrogen, $C_1$–$C_3$ alkyl, phenyl or substituted phenyl, wherein said substituent is one or more $C_1$–$C_4$ alkyl, chloro or cyano groups; and a mineral acid having a first dissociation constant of not less than $1.5 \times 10^{-2}$ at 25° C.

2. The process of claim 1, wherein said hydrogen peroxide is present in an amount of 1–6 moles per mole of formyl group.

3. The process of claim 1, wherein the total of said mineral acid and organic acid is in an amount of from 0.5 to 10 moles per mole of N-formyl-aspartame.

4. The process of claim 1, wherein the time of reaction is 2–40 hours at a temperature of 10° C. to the boiling point of the mixture.

5. The process of claim 1, wherein after the deformylation reaction, the α-isomer is separated by diluting the reaction mixture with water, separating the aqueous phase therefrom, adjusting the pH to about 4.5–5.0 and collecting precipitated aspartame therefrom.

6. The process of claim 1, wherein said organic acid is formic acid or m-chlorobenzoic acid.

7. The process of claim 6, wherein said organic acid is formic acid.

8. The process of claim 1, wherein said mineral acid is hydrochloric, sulfuric or phosphoric acid.

9. The process of claim 8, wherein said mineral acid is phosphoric acid.

* * * * *